(12) United States Patent
Lin et al.

(10) Patent No.: US 12,128,159 B2
(45) Date of Patent: Oct. 29, 2024

(54) ILLUMINATION LAMP SYSTEM HAVING AUTOMATIC SWITCHING FUNCTION FOR STERILIZATION

(71) Applicants: Shih Fong Lin, Taoyuan (TW); Wu Yi Hsu, Taoyuan (TW); Chia-Hsien Chou, Taoyuan (TW)

(72) Inventors: Shih Fong Lin, Taoyuan (TW); Wu Yi Hsu, Taoyuan (TW); Chia-Hsien Chou, Taoyuan (TW)

(73) Assignee: Wu Yi Hsu, Taoyuan (TW)

( * ) Notice: Subject to any disclaimer, the term of this patent is extended or adjusted under 35 U.S.C. 154(b) by 745 days.

(21) Appl. No.: 17/220,662

(22) Filed: Apr. 1, 2021

(65) Prior Publication Data
US 2022/0047761 A1    Feb. 17, 2022

(30) Foreign Application Priority Data
Aug. 12, 2020 (TW) ................. 109127344

(51) Int. Cl.
*A61L 9/20* (2006.01)
(52) U.S. Cl.
CPC ............ *A61L 9/20* (2013.01); *A61L 2209/111* (2013.01); *A61L 2209/12* (2013.01)

(58) Field of Classification Search
CPC ........ A61L 9/20; A61L 2/10; A61L 2209/111; A61L 2209/12; A61L 2209/11; F21V 33/00; F21V 23/0471
See application file for complete search history.

(56) References Cited

U.S. PATENT DOCUMENTS

2019/0192710 A1 * 6/2019 Andersson ............. H05B 47/16

* cited by examiner

*Primary Examiner* — Maris R Kessel
*Assistant Examiner* — Brendan A Hensel
(74) *Attorney, Agent, or Firm* — Ying-Ting Chen; Law Office of Michael Chen

(57) ABSTRACT

An illumination lamp system having automatic switching function for sterilization is disclosed. It contains a plurality of germicidal lighting lamp assemblies, a personnel counter, a data receiving indicator, and an ultraviolet indicator. Each germicidal lighting lamp assembly includes a lamp panel, an infrared human body sensor and a control module. The control module includes a power conversion unit, a synchronization interface, a startup circuit, a first microcontroller, and an output and input connection interface. Because the infrared human body sensor can detect the appearance of people in real time, with a synchronous voltage to switch emitting between illumination LED strips and ultraviolet germicidal light sources, in addition to effectively expanding the disinfection area, it can also safely adjust the type of light to achieve the automatic switching function for sterilization.

18 Claims, 9 Drawing Sheets

ILLUMINATION LAMP SYSTEM HAVING AUTOMATIC SWITCHING FUNCTION FOR STERILIZATION

FIELD OF THE INVENTION

The present invention relates to an illumination lamp. More particularly, the present invention relates to an illumination lamp system having automatic switching function for sterilization.

BACKGROUND OF THE INVENTION

Ultraviolet light has a great disinfection and sterilization effect on bacteria and viruses that are harmful to the human body. The principle of this disinfection and sterilization is that after bacteria and viruses are irradiated with ultraviolet light, the structure of deoxyribonucleic acid (DNA) and ribonucleic acid (RNA) at the core of their lives will be directly destroyed by ultraviolet light, thereby making proteins necessary for survival or reproduction unable to form, causing immediate death of the bacteria and viruses or loss of reproductive capacity. Generally speaking, this kind of disinfection and sterilization effect can be achieved within 1 to 2 seconds after ultraviolet light irradiation. However, there are good things and bad things. Ultraviolet light can eliminate bacteria and viruses that are harmful to humans, and it can also cause harm to humans. for example, under ultraviolet light exposure, human skin will gradually produce melanin. If the duration and frequency of exposure increase, it may lead to the occurrence of melanoma. Ultraviolet light can damage the crystals of the eyes and the portion around the eyes, easily leading to skin cancer around the eyes, and degeneration and degeneration of the retina. In severe cases, it is more likely to cause damage to the transparency of the crystals and cause blindness. Therefore, when the ultraviolet light is used to disinfect the environment, it should pay more attention to safety.

Traditionally, there are two ways to disinfect and sterilize ambient air with ultraviolet light: indirect irradiation method and direct irradiation method. The former diverts the air to the vicinity of the ultraviolet light source, and then returns it to the environment after irradiation to complete disinfection and sterilization with no ultraviolet light irradiating to the human body. The latter is directly sterilized by ultraviolet light in an unmanned and open environment. Both methods have their pros and cons. If indirect irradiation is required, it must rely on additional air guidance equipment, which is not widely used. If direct irradiation is applied, it has to make sure that no one is within the range of UV irradiation. On the other hand, if it needs to irradiate the environment with ultraviolet light, the equipment applied must be large and occupy the existing power supply resource. A compromise way is to combine the existing lamps the equipment, while supplying the illuminating light at the same time for UV disinfection and sterilization. UV disinfection and sterilization are processed along with the supply of illuminating light. A prior art is disclosed as the Taiwan utility patent No. M513332. However, the application scope of the design is still limited to the field of air circulation.

Therefore, in order to solve the inherent problems of the indirect irradiation method and the direct irradiation method while being able to provide indoor ambient lighting and a wide range of ultraviolet light for disinfection and sterilization, the present invention is proposed.

SUMMARY OF THE INVENTION

This paragraph extracts and compiles some features of the present invention; other features will be disclosed in the follow-up paragraphs. It is intended to cover various modifications and similar arrangements included within the spirit and scope of the appended claims.

In order to solve the aforementioned problems, an illumination lamp system having automatic switching function for sterilization is disclosed. The system includes a plurality of germicidal lighting lamp assemblies and is characterized in that each germicidal lighting lamp assembly comprises: a lamp panel, having a plurality of illumination LED strips and at least one ultraviolet germicidal light source arranged on one side, and a plurality of light guide plates protruding outward formed around; an infrared human body sensor, fixed on the outermost edge of one of the light guide plates, being actuated to detect infrared light sources within a detection range and determining whether someone exists based on the detection results; and a control module, installed on the other side of the lamp panel, comprising: a power conversion unit, electrically connected to a power switch externally, receiving AC power from the power switch and performing voltage reduction and conversion to obtain a working AC power and a working DC power when the power switch is turned on; a synchronization interface, electrically connected to the synchronization interface of the control module in other germicidal lighting lamp assemblies, keeping a synchronous voltage between a first electric potential and a second electric potential; a startup circuit, electrically connected to the power conversion unit, the illumination LED strips and the at least one ultraviolet germicidal light source, receiving the working AC power to drive the illumination LED strips and the at least one ultraviolet germicidal light source to light on; and a first microcontroller, electrically connected to the infrared human body sensor, the power conversion unit and the synchronization interface, receiving the working DC power to perform the following tasks: driving the illumination LED strips to light on via the startup circuit, and keeping the synchronous voltage at the first electric potential; after the illumination LED strips have been lighted on for a first waiting time, turning off the illumination LED strips and driving the at least one ultraviolet germicidal light source to light on via the startup circuit, actuating the infrared human body sensor to detect, and changing the synchronous voltage to the second electric potential; when the infrared human body sensor determines that there are someone, turning off the at least one ultraviolet germicidal light source and driving the illumination LED strips to light on via the startup circuit, and changing the synchronous voltage to the first electric potential; and when the infrared human body sensor determines that there are no one and after the illumination LED strips have been lighted on for the first waiting time, turning off the illumination LED strips and driving the at least one ultraviolet germicidal light source to light on via the startup circuit, and changing the synchronous voltage to the second electric potential. When the synchronous voltage of the synchronization interface of any one of the germicidal lighting lamp assemblies is changed from the second electric potential to the first electric potential, the synchronous voltage of the synchronization interface of other germicidal lighting lamp assemblies is changed accordingly.

Another illumination lamp system having automatic switching function for sterilization is still disclosed in the present invention. It includes a plurality of germicidal lighting lamp assemblies and is characterized in that: each germicidal lighting lamp assembly comprises: a lamp panel, having a plurality of illumination LED strips and at least one ultraviolet germicidal light source arranged on one side, and a plurality of light guide plates protruding outward formed around; and a control module, installed on the other side of the lamp panel, comprising: a power conversion unit, electrically connected to a power switch externally, receiving AC power from the power switch and performing voltage reduction and conversion to obtain a working AC power and a working DC power when the power switch is turned on; a startup circuit, electrically connected to the power conversion unit, the illumination LED strips and the at least one ultraviolet germicidal light source, receiving the working AC power to drive the illumination LED strips and the at least one ultraviolet germicidal light source to light on; and a first microcontroller, electrically connected to the power conversion unit and the startup circuit, receiving the working DC power to perform the following tasks: driving the illumination LED strips to light on via the startup circuit when the power switch is on; when the power switch is turned off and turned on within 3 seconds in an on state, turning off the illumination LED strips and driving the at least one ultraviolet germicidal light source to light on for a set time via the startup circuit; and when the at least one ultraviolet germicidal light source has been lighted for the set time, turning off the at least one ultraviolet germicidal light source and driving the illumination LED strips to light on via the startup circuit.

Preferably, the ultraviolet germicidal light source may be an ultraviolet LED light bar, a strip ultraviolet germicidal lamp or a ring ultraviolet germicidal lamp.

In one embodiment, startup circuit may further comprise: a first relay, electrically connected to the first microcontroller and the power conversion unit, controlled by the first microcontroller to switch to transmit the working AC power; a first illumination LED strip driver, electrically connected to the first relay and the illumination LED strips, regulating the working AC power to drive the illumination LED strips to light on; a second relay, electrically connected to the first microcontroller and the power conversion unit, controlled by the first microcontroller to switch to transmit the working AC power; and a first ultraviolet germicidal light source driver, electrically connected to the second relay and the at least one ultraviolet germicidal light source, regulating the working AC power to drive the at least one ultraviolet germicidal light source to light on.

In another embodiment, the startup circuit may further comprise: a third relay, electrically connected to the first microcontroller and the power conversion unit, controlled by the first microcontroller to switch to transmit the working AC power; a second illumination LED strip driver, electrically connected to the third relay and the illumination LED strips, regulating the working AC power to drive the illumination LED strips to light on; and a second ultraviolet germicidal light source driver, electrically connected to the third relay and the at least one ultraviolet germicidal light source, regulating the working AC power to drive the at least one ultraviolet germicidal light source to light on. The third relay only transmits the working AC power to one of the second illumination LED strip driver and the second ultraviolet germicidal light source driver.

In still another embodiment, the startup circuit may further comprise: a driver, electrically connected to the power conversion unit, converting the working AC power to a driving DC power which is able to drive the illumination LED strips or the at least one ultraviolet germicidal light source to light on; and a fourth relay, electrically connected to the first microcontroller, the driver, the illumination LED strips and the at least one ultraviolet germicidal light source, controlled by the first microcontroller to switch to transmit the working AC power to the illumination LED strips or the at least one ultraviolet germicidal light source.

According to the present invention, each germicidal lighting lamp assembly may further comprise an output and input connection interface, electrically connected to the first microcontroller, signally connecting to a control device externally for adjusting functions of the first microcontroller by the control device.

Preferably, the output and input connection interface may be a USB connector, a RJ10 connector, a RJ45 connector or an infrared signal transceiver module.

According to the present invention, the first microcontroller is controlled by the control device to perform the following tasks: setting a scheduled running time for the at least one ultraviolet germicidal light source; setting a total luminous time of the at least one ultraviolet germicidal light source in the scheduled running time; and setting electrical connection between one synchronization interface and the synchronization interface of the control module in other germicidal lighting lamp assembly to create a group, or cutting off electrical connection of synchronization interfaces of the control modules of the germicidal lighting lamp assemblies to abolish an existing group. The first microcontroller further turns off the at least one ultraviolet germicidal light source and drives the illumination LED strips to light on via the startup circuit, and changes the synchronous voltage to the first electric potential after the total luminous time of the at least one ultraviolet germicidal light source in the scheduled running time has passed.

Preferably, the scheduled running time is greater than or equal to 2 hours.

Preferably, the first microcontroller of each germicidal lighting lamp assembly further stores a serial number.

The aforementioned illumination lamp system having automatic switching function for sterilization further includes a control circuit. The control circuit is electrically connected to the first microcontroller of each germicidal lighting lamp assembly, detects the serial number of each germicidal lighting lamp assembly, checks whether the germicidal lighting lamp assembly is in one group, and send the results of detection to a monitor signally connected thereto. The first microcontroller of each germicidal lighting lamp assembly may further store operation sequence of the at least one ultraviolet germicidal light source.

According to the present invention, the control device may further comprise: at least one signal connection interface, signally connected to the output and input connection interface; a display screen; an input module; a plurality of status indicators; and a second microcontroller, electrically connected to the at least one signal connection interface, the display screen, the input module and the plurality of status indicators, showing functions and options thereof of the first microcontroller required to be adjusted on the display screen, setting the options of the functions of the first microcontroller that need to be adjusted via the input module, sending the options of the functions of the first microcontroller that need to be adjusted to the first microcontroller via the at least one signal connection interface, and showing current usage status of the control device via the status indicators.

According to the present invention, a data receiving indicator may be installed on the lamp panel. The data receiving indicator is electrically connected to the first microcontroller, When the first microcontroller receives data via the output and input connection interface, the first microcontroller activates the data receiving indicator.

Preferably, the synchronization interface may be a power line contact.

Said illumination lamp system having automatic switching function for sterilization may further include a personnel counter, signally connected to the first microcontroller of the control module, counting the number of people in the space where all germicidal lighting lamp assemblies are located. If a count of the personnel counter increases while the synchronous voltage still remains at the second electric potential, the first microcontroller turns off the at least one ultraviolet germicidal light source and drives the illumination LED strips to light on via the startup circuit, and changes the synchronous voltage to the first electric potential.

Said illumination lamp system having automatic switching function for sterilization may further include an ultraviolet indicator, signally connected to the first microcontroller of the control module. When the ultraviolet germicidal light sources are lighted on, the first microcontroller activates the ultraviolet indicator.

Because the infrared human body sensor can detect the appearance of people in real time, with a synchronous voltage to switch emitting between illumination LED strips and ultraviolet germicidal light sources, in addition to effectively expanding the disinfection area, it can also safely adjust the type of light. At the same time, it also solves the inherent problems in the indirect irradiation method and the direct irradiation method.

DETAILED DESCRIPTION OF THE PREFERRED EMBODIMENTS

The present invention will now be described more specifically with reference to the following embodiments.

Figure 1:
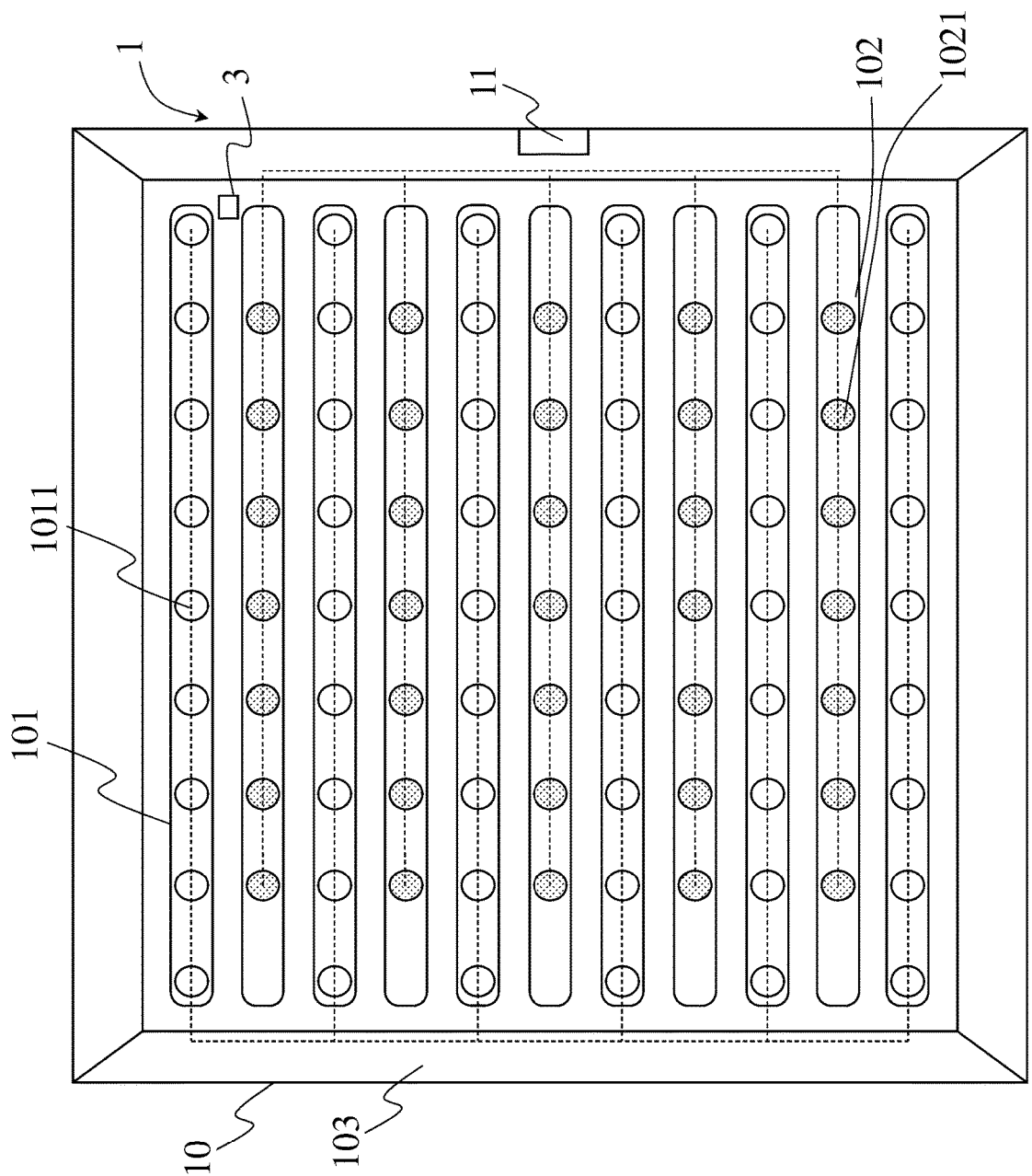
FIG. 1 is a schematic diagram of a lamp panel of an illumination lamp system having automatic switching function for sterilization according to an embodiment of the present invention.
Figure 2:
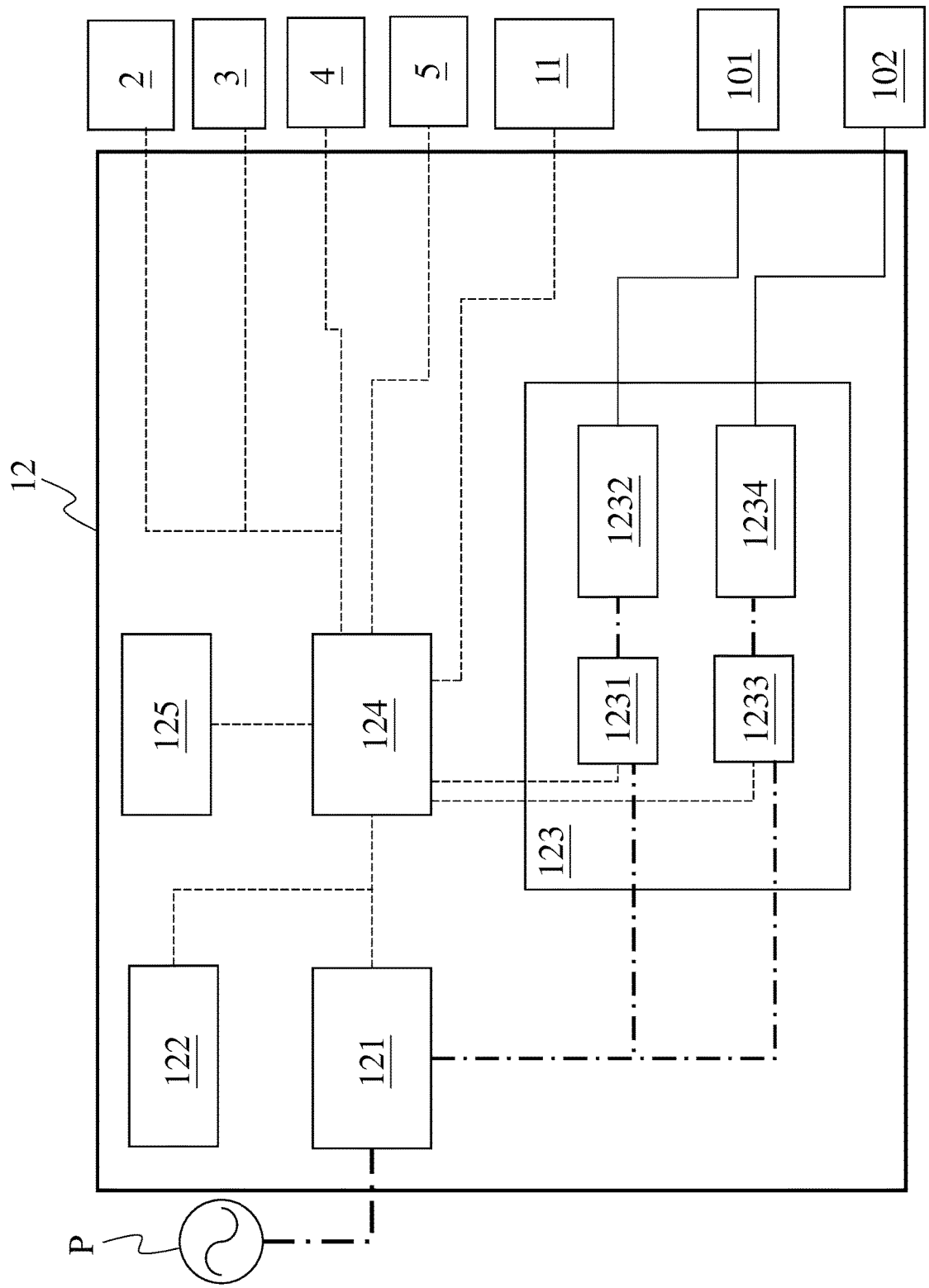
FIG. 2 is a circuit diagram of some parts of the illumination lamp system having automatic switching function for sterilization.

Please see FIG. 1 and FIG. 2. FIG. 1 is a schematic diagram of a lamp panel of an illumination lamp system having automatic switching function for sterilization (hereinafter referred to as the system) according to an embodiment of the present invention. FIG. 2 is a circuit diagram of some parts of the system. The system includes a number of germicidal lighting lamp assembly 1, a personnel counter 2, a data receiving indicator 3, and an ultraviolet indicator 4. According to the present invention, the structure and function of each germicidal lighting lamp assembly 1 are the same, only the difference in the layout. Therefore, FIG. 2 only shows part of the circuit of one germicidal lighting lamp assembly 1 for illustration. The remaining circuit and the appearance are shown in FIG. 1. The following is an explanation of the structure, function, interaction and operation of each technical component of the system.

Each germicidal lighting lamp assembly 1 include a lamp panel 10, an infrared human body sensor 11 and a control module 12. The lamp panel 10 is a carrier for mounting light-emitting components and related electronic components. Generally speaking, the size of the lamp panel 10 is not limited, as long as it can be effectively installed in the space that needs to be disinfected and can provide the amount of light required by people for their activities. According to the present invention, preferably, the lamp panel 10 can meet the existing appearance specifications of light steel frame lamps, for example, having the appearance of a square with a side length of 60 cm, or a rectangle with 60 cm on one side and 120 cm on the other side. In this embodiment, the former is used for illustration. A number of illumination LED strips 101 and at least one ultraviolet germicidal light source 102 are arranged on one side (illuminated side) of the lamp panel 10. According to the present invention, the ultraviolet germicidal light source 102 may be, but not limited to an ultraviolet LED light bar, a strip ultraviolet germicidal lamp or a ring ultraviolet germicidal lamp. In the present embodiment, 5 ultraviolet LED light bars are used as the example of the ultraviolet germicidal light sources 102 for illustration. They are arranged alternately with 6 illumination LED strips 101. There are some visible LEDs 1011 in the illumination LED strip 101. They are the main body used by the system to provide illuminating light. In terms of specifications, they can emit red, blue, green and other single narrow-range wavelength color light, or they can emit multi-range wavelength synthetic light as needed, for example, white light. Due to the advancement of technology, the visible LEDs 1011 may be the diode lamp beads using DC power. They can also be the diode lamp beads using AC power. The illumination LED strips 101 has the advantages of power saving and durability compared with general light emitting sources.

Relatively, the ultraviolet germicidal light sources 102 (ultraviolet LED light bars) are the main body of the system to provide the functions of disinfection and sterilization. Different from the illumination LED strips 101, the ultraviolet light LEDs 1021 of the ultraviolet LED light bars emit ultraviolet light that is invisible to the naked eye, but it can effectively kill a certain proportion of viruses and bacteria within a certain range. The same function can be achieved by using strip ultraviolet germicidal lamps or ring ultraviolet germicidal lamps. The ultraviolet light LEDs 1021 can be diode lamp beads that use DC power or diode lamp beads that use AC power. The illumination LED strips 101 and the ultraviolet germicidal light sources 102 are arranged in a staggered manner. The purpose is to make the germicidal lighting lamp assembly 1 emit light more evenly. However, the staggered layout is not limited to one-to-one interlacing between the two. In practice, the interleaving of the illumination LED strips 101 and the ultraviolet germicidal light sources 102 can be one-to-two, two-to-one, two-to-two, etc. A number of light guide plates 103 are protruding outward and formed around the lamp panel 10. The light guide plate 103 is a tool that reflects the light emitted by the illumination LED strips 101 and the ultraviolet germicidal light sources 102 downward and concentrates it in a specific area. The outer part of the lamp panel 10 is more protruding from the illumination LED strips 101 and the ultraviolet germicidal light sources 102 (after installing germicidal lighting lamp assembly 1 on the light steel frame, the closer the part is to the ground). The light guide plate 103 can provide visible light in the specific area, and can also bring disinfection and sterilization ultraviolet light to the specific area. In the present embodiment, Because the lamp panel 10 has a square appearance, there 4 light guide plates 103.

The infrared human body sensor 11 is fixed on the outermost edge of one of the light guide plates 103. Its function is to detect infrared light sources within a detection range after it is actuated and determines whether someone exists based on the detection results. There are many types of existing infrared human body sensors, and the present invention does not limit the brands and models to be used.

The control module 12 is installed on the other side of the lamp panel 10 (non-illuminated side) and includes a power conversion unit 121, a synchronization interface 122, a startup circuit 123, a first microcontroller 124 and an output and input connection interface 125. The power conversion unit 121 is electrically connected to a power switch P, externally. When the power switch P is turned on, the power conversion unit 121 receives AC power from the power switch P and performs voltage reduction and conversion, to obtain a working AC power and a working DC power. In practice, the power switch P can be connected to the contact (socket) of the power grid. The power conversion unit 121 is a circuit design that converts the AC power of the power grid into the working AC power and the working DC power required by the various components of the system. According to requirements, the power conversion unit 121 can include an AC-to-DC module and a transformer, and can output the working AC power and the working DC power separately. The synchronization interface 122 is electrically connected to the synchronization interface 122 of the control module 12 in other germicidal lighting lamp assemblies 1, keeping a synchronous voltage between a first electric potential and a second electric potential. Here, the first electric potential and the second electric potential are relative; one is high, the other is relatively low. If the first electric potential is high electric potential, the second electric potential is low electric potential. Relatively, if the second electric potential is high electric potential, the first electric potential is low electric potential. The synchronization interface 122 is a tool to control the germicidal lighting lamp assembly 1 by changing the voltage value to the first electric potential or the second electric potential to turn on the illumination LED strips 101 or ultraviolet germicidal light sources 102 synchronously. Therefore, the synchronization interface 122 can basically be a power line contact. The synchronization method of the synchronization interface 122 will be explained later.

The startup circuit 123 is electrically connected to the power conversion unit 121, the illumination LED strips 101 and the ultraviolet germicidal light sources 102. The startup circuit 123 can receive the working AC power to drive the illumination LED strips 101 and the ultraviolet germicidal light sources 102 to light on. It is a component that can emit visible light or ultraviolet light separately. The startup circuit 123 can have different designs according to the output power of the germicidal lighting lamp assembly 1. In the following, different embodiments are used for illustration.

Please see FIG. 2 again. In one embodiment, the startup circuit 123 may include a first relay 1231, a first illumination LED strip driver 1232, a second relay 1233 and a first ultraviolet germicidal light source driver 1234. It should be noted that the form of relay used in the present invention is not limited. Preferably, it can be a solid relay. In addition, for the sake of convenience, the thick dotted and dashed lines indicate the lines the working AC power goes through. The thin dashed lines indicate the lines the working DC power goes through. The thin solid lines indicate the lines that can pass DC or AC power after conversion. The first relay 1231 is electrically connected to the first microcontroller 124 and power conversion unit 121. The first relay 1231 is controlled by the first microcontroller 124 to switch to transmit the working AC power. The first illumination LED strip driver 1232 is electrically connected to the first relay 1231 and all illumination LED strips 101. Its function is to regulate the working AC power to drive the illumination LED strips 101 to light on. The second relay 1233 is electrically connected to the first microcontroller 124 and the power conversion unit 121. The second relay 1233 is controlled by the first microcontroller 124 to switch to transmit the working AC power. The first ultraviolet germicidal light source driver 1234 is electrically connected to the second relay 1233 and all ultraviolet germicidal light sources 102, regulating the working AC power to drive the ultraviolet germicidal light sources 102 to light on.

Figure 3:
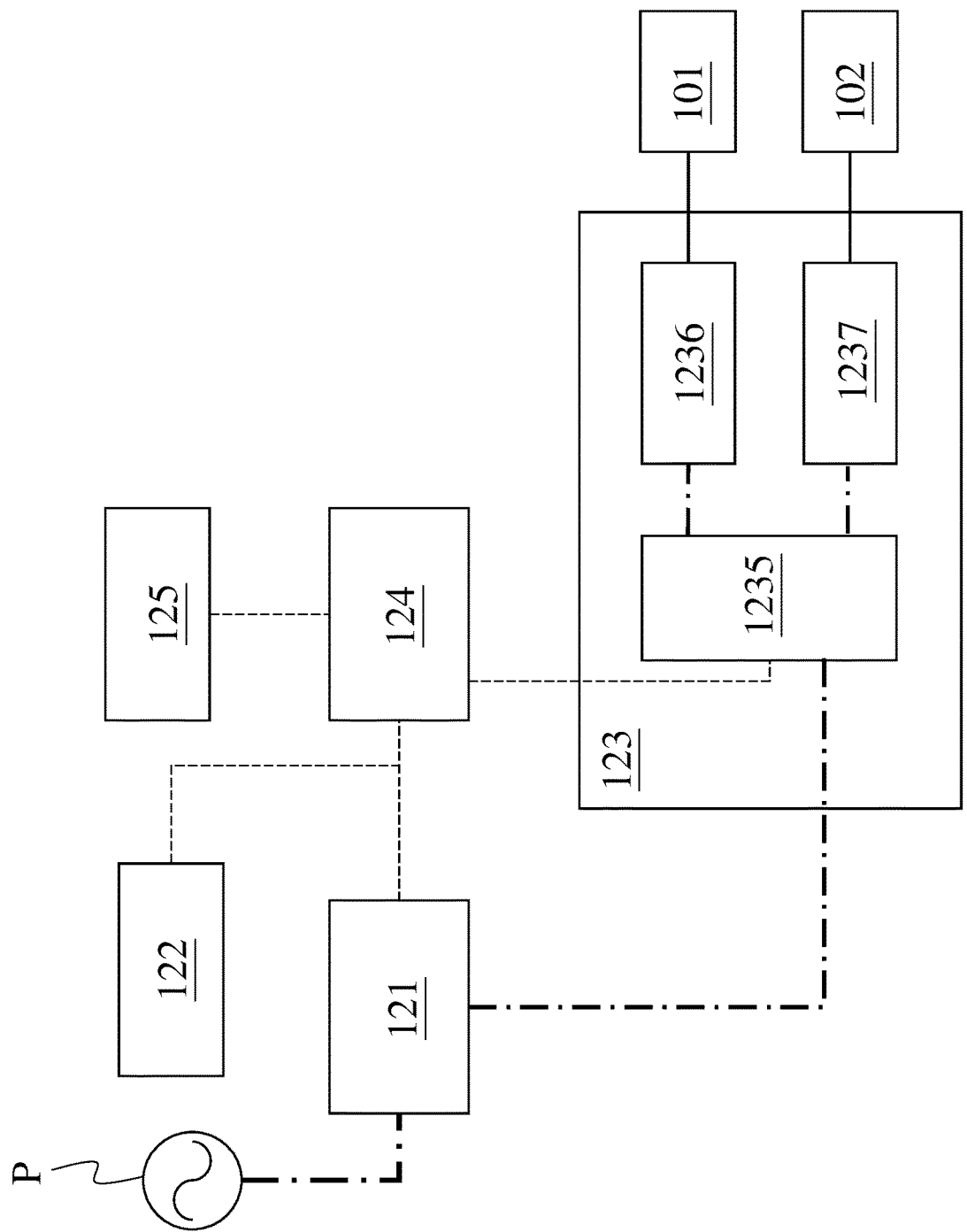
FIG. 3 is another circuit diagram of some parts of the illumination lamp system having automatic switching function for sterilization.

Please see FIG. 3. In another embodiment, the startup circuit 123 may include a third relay 1235, a second illumination LED strip driver 1236 and a second ultraviolet germicidal light source driver 1237. The third relay 1235 is electrically connected to the first microcontroller 124 and the power conversion unit 121. The third relay 1235 is controlled by the first microcontroller 124 to switch to transmit the working AC power. The third relay 1235 only transmits the working AC power to one of the second illumination LED strip driver 1236 and the second ultraviolet germicidal light source driver 1237. The second illumination LED strip driver 1236 is electrically connected to the third relay 1235 and all illumination LED strips 101, regulating the working AC power to drive the illumination LED strips 101 to light on. Relatively, the second ultraviolet germicidal light source driver 1237 is electrically connected to the third relay 1235 and all ultraviolet germicidal light sources 102, regulating the working AC power to drive the ultraviolet germicidal light sources 102 to light on.

Figure 4:
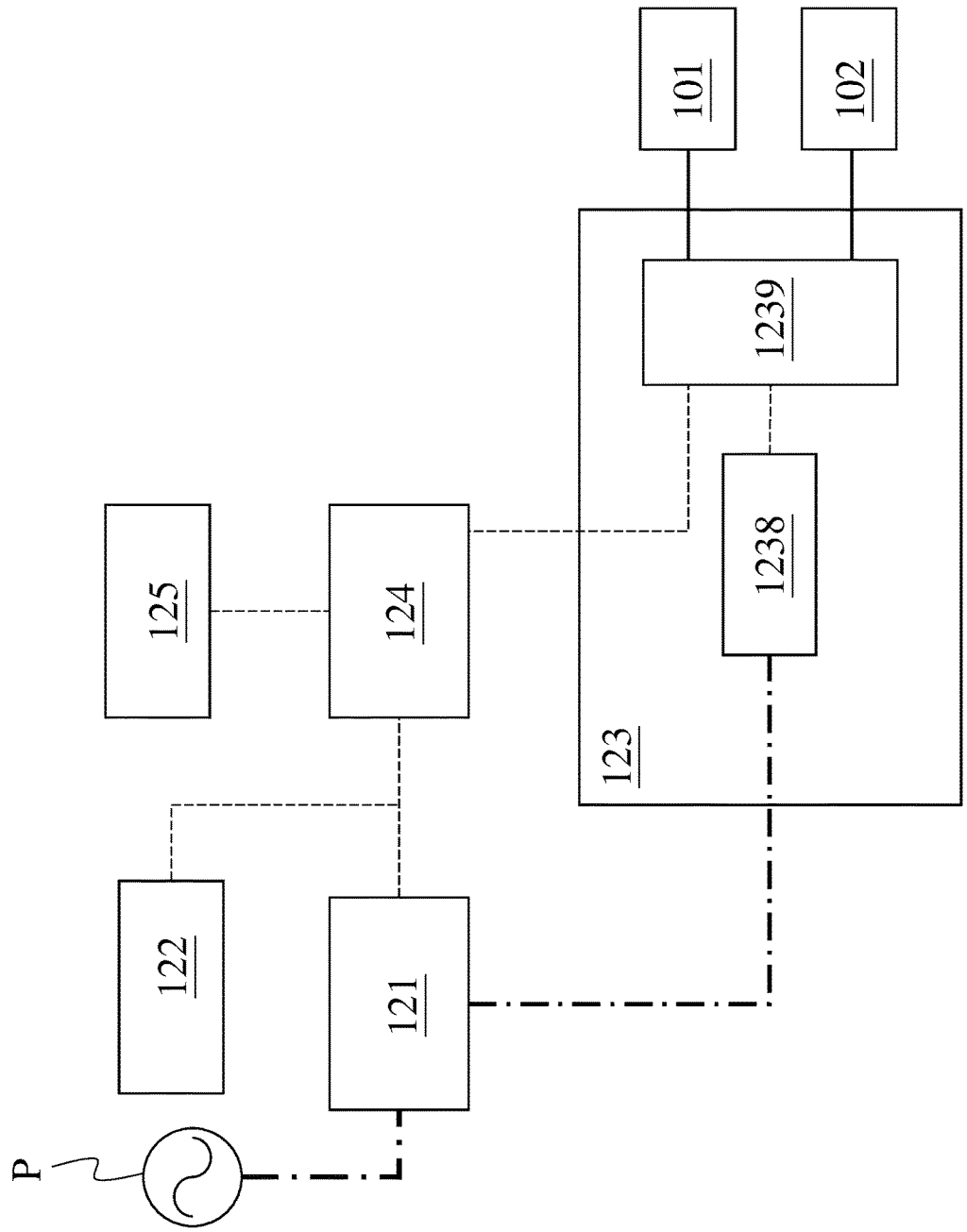
FIG. 4 is still another circuit diagram of some parts of the illumination lamp system having automatic switching function for sterilization.

Please refer to FIG. 4. In another embodiment, the startup circuit 123 may include a driver 1238 and a fourth relay 1239. The driver 1238 is electrically connected to the power conversion unit 121. It can convert the working AC power to a driving DC power which is able to drive all illumination LED strips 101 or all ultraviolet germicidal light sources 102 to light on. The fourth relay 1239 is electrically connected to the first microcontroller 124, the driver 1238, the illumination LED strips 101 and the ultraviolet germicidal light sources 102. The fourth relay 1239 is controlled by the first microcontroller 124 to switch to transmit the working AC power to the illumination LED strips 101 or the ultraviolet germicidal light sources 102.

The first microcontroller 124 is electrically connected to the infrared human body sensor 11, the power conversion unit 121 and the synchronization interface 122. This is also the main component of the system that can "automatically switch disinfection and sterilization". The first microcontroller 124 can receive the working DC power to perform the following tasks: first, driving all illumination LED strips 101 to light on via the startup circuit 123 and keeping the synchronous voltage at the first electric potential (start/reset operation); second, after the illumination LED strips 101 have been lighted on for a first waiting time, turning off the illumination LED strips 101 and driving the ultraviolet germicidal light sources 102 to light on via the startup circuit 123, actuating the infrared human body sensor 11 to detect, and changing the synchronous voltage to the second electric potential (sterilization operation); third, when the infrared human body sensor 11 determines that there are someone, turning off the ultraviolet germicidal light sources 102 and driving the illumination LED strips 101 to light on via the startup circuit 123, and changing the synchronous voltage to the first electric potential (light resupply operation); and fourth, when the infrared human body sensor 11 determines that there are no one and after the illumination LED strips 101 have been lighted on for the first waiting time, turning off the illumination LED strips 101 and driving the ultraviolet germicidal light sources 102 to light on via the startup circuit 123, and changing the synchronous voltage to the second electric potential (re-sterilization operation). The aforementioned four tasks can be automatically executed under the operation of the first microcontroller 124, so this embodiment is a fully automatic structure.

Figure 5:
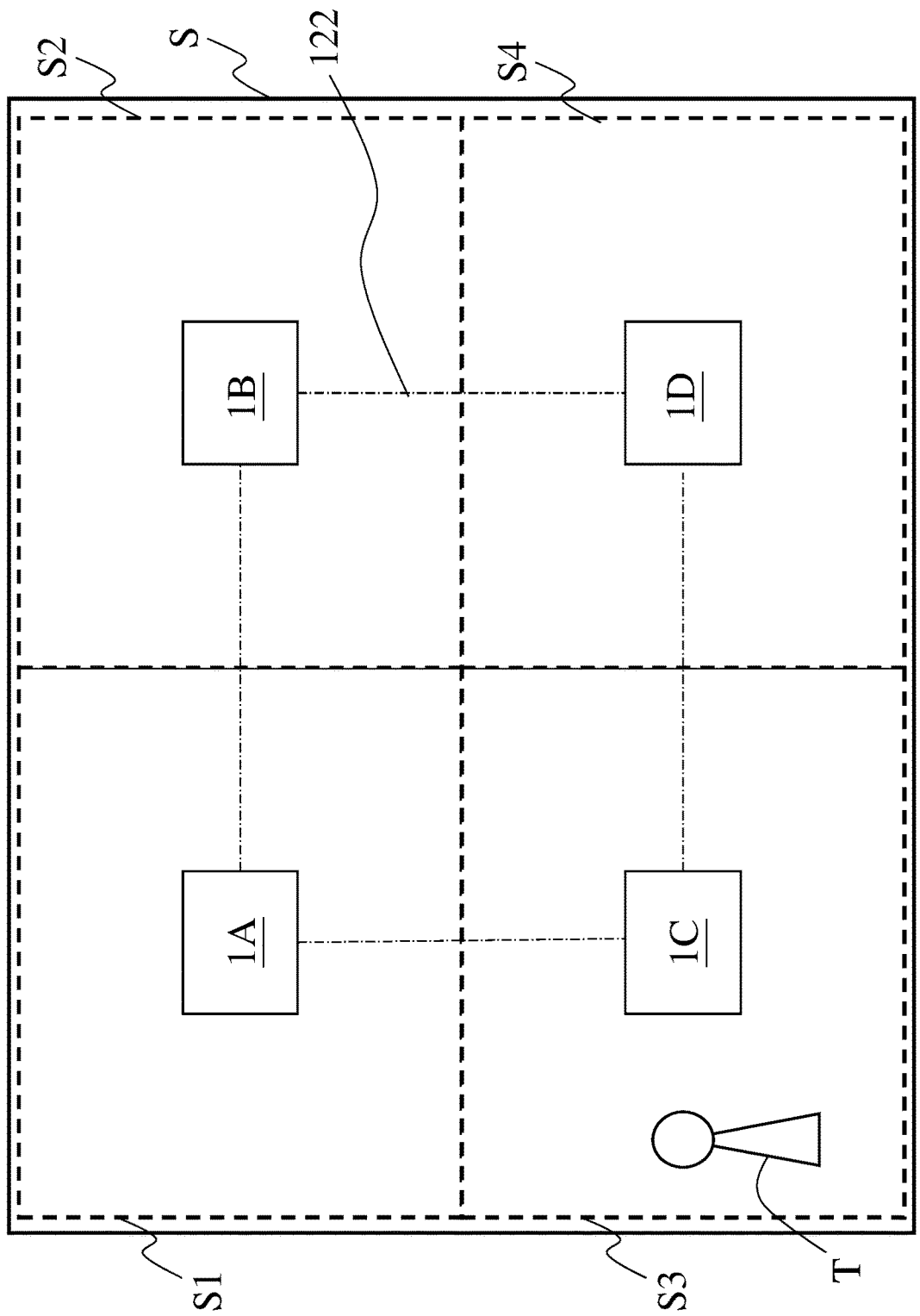
FIG. 5 shows the configuration of the illumination lamp system having automatic switching function for sterilization.

In order to have a better understanding of the above tasks and synchronous operation methods, please see FIG. 5. It shows the configuration of the system. In a space S that needs to be disinfected, 4 germicidal lighting lamp assemblies (a first germicidal lighting lamp assembly 1A, a second germicidal lighting lamp assembly 1B, a third germicidal lighting lamp assembly 1C and a fourth germicidal lighting lamp assembly 1D) are installed. The synchronization interfaces 1224 of the germicidal lighting lamp assembly are electrically connected. The first germicidal lighting lamp assembly 1A are used to sterilize a first subspace S1, the second germicidal lighting lamp assembly 1B are used to sterilize a second subspace S2, the third germicidal lighting lamp assembly 1C are used to sterilize a third subspace S3, and the fourth germicidal lighting lamp assembly 1D are used to sterilize a fourth subspace S4. The first subspace S1, the second subspace S2, the third subspace S3, and the fourth subspace S4 together are space S. In the start/reset operation, as long as the power switch P is turned on, the illumination LED strips 101 of the 4 germicidal lighting lamp assemblies will all light up to provide the light required by space S. This is a preset step. The sterilization operation is after the start/the start/reset operation, when the first waiting time has passed, the ultraviolet germicidal light sources 102 of the germicidal lighting lamp assemblies 1 will automatically emit light for sterilization, and turn off the illumination LED strips 101. In practice, the first waiting time may be 5 minutes, 10 minutes, or 15 minutes. The purpose is to confirm that there is no one in the space where needs to be sterilized. For some existing infrared human body sensor, when the human body is not moving, for example, when a patient in a hospital is moved to a ward on bed, it is impossible to determine whether there is someone in the space. Therefore, the first waiting time can be set longer or shorter according to actual needs and the characteristics of the infrared human body sensor 11.

The purpose of changing the synchronous voltage from the first electric potential to the second electric potential is to let other connected germicidal lighting lamp assemblies in the same space know that there is no one in the subspace where the germicidal lighting lamp assembly sending the message is located. According to the present invention, when the synchronous voltage of the synchronization interface 122 of any one of the germicidal lighting lamp assemblies is changed from the second electric potential to the first electric potential, the synchronous voltage of the synchronization interface 122 of other germicidal lighting lamp assemblies is changed accordingly. But when the synchronous voltage changes from the first electric potential to the second electric potential, if not all the synchronous voltages of the synchronization interface 122 of the germicidal lighting lamp assemblies are at the second electric potential, after changing the electric potential, the synchronous voltage of the synchronization interface 122 of the germicidal lighting lamp assemblies must be reset to the first electric potential. In other words, only when all the infrared human body sensors 11 of the germicidal lighting lamp assemblies have not detected the presence of someone in the subspace they are in charge of, the synchronous voltage will be at the second electric potential for sterilization. The light resupply operation is to stop the ultraviolet light sterilization operation when the infrared human body sensor 11 of some germicidal lighting lamp assembly finds that there is someone. Please refer to FIG. 5. When all germicidal lighting lamp assemblies are in sterilization operation, the synchronous voltage of the connected synchronization interfaces 122 is at the second electric potential. When a user T enters the third subspace S3 and the infrared human body sensor 11 of the third germicidal lighting lamp assembly 1C finds the user T, the first microcontroller 124 of the third germicidal lighting lamp assemblies 1C changes the synchronous voltage from second electric potential to first electric potential. Synchronously, the synchronous voltage of the first germicidal lighting lamp assembly 1A, the second germicidal lighting lamp assembly 1B and the fourth germicidal lighting lamp assembly 1D also becomes first electric potential. At this time, all germicidal lighting lamp assembly enter the light resupply operation. At last, the re-sterilization operation is to continue disinfection after user T leaves space S and each germicidal lighting lamp assembly has passed the first waiting time again.

Figure 6:
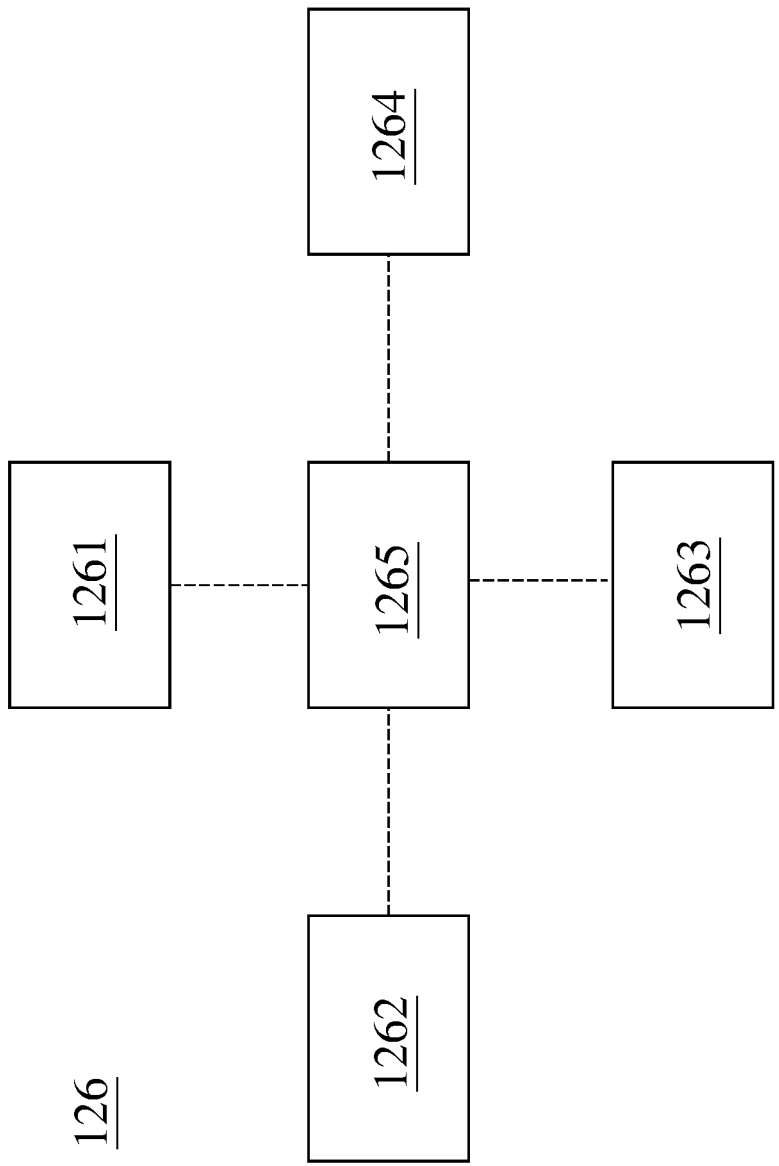
FIG. 6 is a circuit diagram of a control device.
Figure 7:
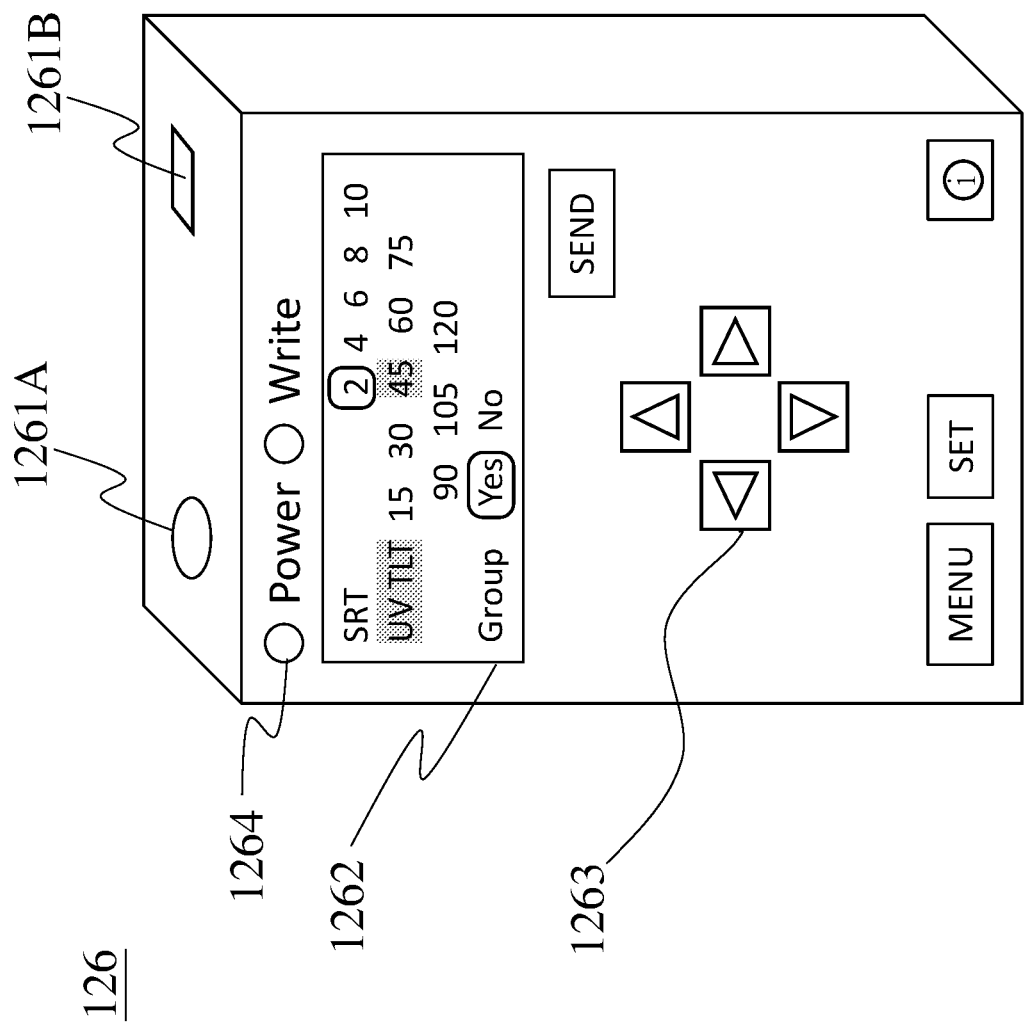
FIG. 7 is a schematic diagram of the control device.

The output and input connection interface 125 is electrically connected to the first microcontroller 124 to signally connecting to a control device 126 externally for adjusting functions of the first microcontroller 124 by the control device 126. In practice, the output and input connection interface 125 may be wired transmission type, for example, a USB connector, a RJ10 connector or a RJ45 connector, or wireless transmission type, for example, an infrared signal transceiver module. Please see FIG. 6 and FIG. 7. FIG. 6 is a circuit diagram of the control device 126. FIG. 7 is a schematic diagram of the control device 126. The control device 126 includes at least one signal connection interface 1261, a display screen 1262, an input module 1263, a number of status indicators 1264 and a second microcontroller 1265. The at least one signal connection interface 1261 is signally connected to the output and input connection interface 125. In the present embodiment, the control device 126 is equipped with a USB signal connection interface 1261A and an infrared signal connection interface 1261B. The former is wiredly signally connected, the latter can be wirelessly signally connected. In other embodiments, the number of the signal connection interface 1261 may be more, or just keep one. The display screen 1262 may be an LCD screen. The input module 1263 can be a set of physical buttons to control the cursor in the display screen 1262 to move up, down, left, and right, select the function to be adjusted (MENU), select option of the function (SET), turn on or turn off the control device 126(*i*), and send the selection (SEND). In the present embodiment, there 2 status indicators 1264 (Power, Write). The second microcontroller 1265 is electrically connected to the at least one signal connection interface 1261, the display screen 1262, input module 1263 and the status indicators 1264, showing functions and options thereof of the first microcontroller 124 required to be adjusted on the display screen 1262, setting the options of the functions of the first microcontroller 124 that need to be adjusted via the input module 1263, sending the options of the functions of the first microcontroller 124 that need to be adjusted to the first microcontroller 124 via the at least one signal connection interface 1261, and showing current usage status of the control device 126 via the status indicators 1264.

According to the present invention, the first microcontroller 124 is controlled by the control device 126 to perform the following tasks: setting a scheduled running time for all ultraviolet germicidal light sources 102 (the time that the ultraviolet germicidal light sources 102 are allowed to emit light in the future); setting a total luminous time of all ultraviolet germicidal light sources 102 in the scheduled running time (setting the total cumulative time of ultraviolet light disinfection and sterilization); and setting electrical connection between one synchronization interface 122 and the synchronization interface 122 of the control module 12 in other germicidal lighting lamp assemblies 1 to create a group, or cutting off electrical connection of synchronization interfaces 122 of the control modules 12 of the germicidal lighting lamp assembly 1 to abolish an existing group (control a germicidal lighting lamp assembly to join or exit a synchronized operation group composed by other germicidal lighting lamp assemblies). The scheduled running time is the concept of a big cycle, specifying the time when ultraviolet germicidal light sources 102 can emit. The total luminous time in the scheduled running time is a concept of a small cycle, requiring the time the ultraviolet germicidal light sources 102 to be intermittent (e.g., when someone enters the sterilization space and ultraviolet germicidal light sources 102 are forced to stop) or continuously luminescent in the scheduled running time to meet the basic needs of sterilization. When setting the scheduled running time, the display screen 1262 of the control device 126 will display the options of the scheduled running time, for example, but not limited to 2, 4, 6, 8, 10 hours, etc. According to the present invention, the scheduled running time may be greater than or equal to 2 hours. If the scheduled running time is set to 8 hours and the total luminous time is set to 45 minutes, it will require each germicidal lighting lamp assembly 1 to take 8 hours as a big cycle, and the total time to drive ultraviolet germicidal light sources 102 to emit light is 45 minutes. If the ultraviolet germicidal light sources 102 stops operating due to an accident for too long and the total luminous time is shorter than 45 minutes, it will not make up for the lack of time after 8 hours. When setting the total luminous time of ultraviolet germicidal light sources 102, the display screen 1262 of the control device 126 will display the option of ultraviolet total time (UV TLT), for example, but not limited to 15, 30, 45, 60, 75, 90, 105, 120 minutes, etc. for selection. When joining or exiting a group of the germicidal lighting lamp assemblies, the display screen 1262 of the control device 126 will display its options, yes (join) and no (exit). After setting, the setting message will be sent out, and the first microcontroller 124 will execute the corresponding options of the functions. In the present embodiment, the display screen 1262 of the control device 126 displays all the functions that need to be adjusted and their corresponding options. As shown in FIG. 7, UV TLT is displayed with shadow. It means that the function that needs to be adjusted is the total luminous time of ultraviolet germicidal light sources 102. The currently selected option is 45 minutes (shown by shadow). The first microcontroller 124 may turns off the ultraviolet germicidal light sources 102 and drive the illumination LED strips 101 to light on via the startup circuit 123, and change the synchronous voltage to the first electric potential after the total luminous time of the ultraviolet germicidal light sources 102 in the scheduled running time has passed. Namely, when the light-on time of the ultraviolet germicidal light sources 102 is over the total luminous time, all germicidal lighting lamp assemblies 1 in the group all return to normal lighting state. The first microcontroller 124 of each germicidal lighting lamp assembly 1 may further store operation sequence of the ultraviolet germicidal light sources 102. Thus, the total luminous time has a calculable basis.

Please see FIG. 2 again. Since the infrared human body sensor 11 may be in the case where the human body is not moving, such as a patient who is pushed into the ward on the hospital bed, it would be misjudged that no one has entered the sterilization space. Therefore, to solve this problem, it is necessary to have fool-proof measures to avoid accidentally hurting people when disinfecting with ultraviolet light. The personnel counter 2 is a foolproof measure. The personnel counter 2 may be installed outside the space where the germicidal lighting lamp assemblies are located (or at the entrance), signally connected to the first microcontroller 124 of the control module 12 by power line, counting the number of people in the space where all germicidal lighting lamp assemblies are located by electronic or manual counting method. If a count of the personnel counter 2 increases while the synchronous voltage of the germicidal lighting lamp assemblies still remains at the second electric potential, the first microcontroller 124 of the germicidal lighting lamp assembly turns off all ultraviolet germicidal light sources 102 and drives all illumination LED strips 101 to light on via the startup circuit 123, and changes the synchronous voltage to the first electric potential. Namely, if none of the germicidal lighting lamp assemblies find that someone enters but the personal counter 2 does, the personnel counter 2 will send out a message to notify all the first microcontrollers 124, so that all germicidal lighting lamp assemblies can be restored to normal light.

A data receiving indicator 3 is installed on the lamp panel 10. The data receiving indicator 3 is electrically connected to the first microcontroller 124. When the first microcontroller 124 receives data via the output and input connection interface 125, the first microcontroller 124 activates the data receiving indicator 3, showing the first microcontroller 124 is in a setting state. The ultraviolet indicator 4 reminds people that a certain area is being sterilized with ultraviolet light. The ultraviolet indicator 4 can be installed in a suitable place, signally connected to the first microcontroller 124 of the control module 12 through the power line. When the ultraviolet germicidal light sources 102 are lighted on, the first microcontroller 124 activates the ultraviolet indicator 4.

According to the present invention, the first microcontroller 124 of germicidal lighting lamp assembly 1 may further store a serial number. The serial numbers of different germicidal lighting lamp assemblies 1 are different. Setting status and group status of a germicidal lighting lamp assembly 1 installed in a specific position can be known according to the serial number. In order to remotely control these germicidal lighting lamp assemblies 1, the system further includes a control circuit 5. As shown in FIG. 2. The control circuit 5 is electrically connected to the first microcontroller 124 of each germicidal lighting lamp assembly 1. It detects the serial number of each germicidal lighting lamp assembly, checks whether the germicidal lighting lamp assembly is in one group, and sends the results of detection to a monitor (not shown) signally connected thereto.

As mentioned earlier, the previous embodiment is a fully automatic structure. According to the present invention, the illumination lamp system having automatic switching function for sterilization may be a semi-automatic structure. That is, just set the sterilization time and start method, and it can continue to sterilize with ultraviolet light regardless of the people entering and exiting. Here is an example with FIG. 8 and FIG. 9 for illustration.

Figure 8:
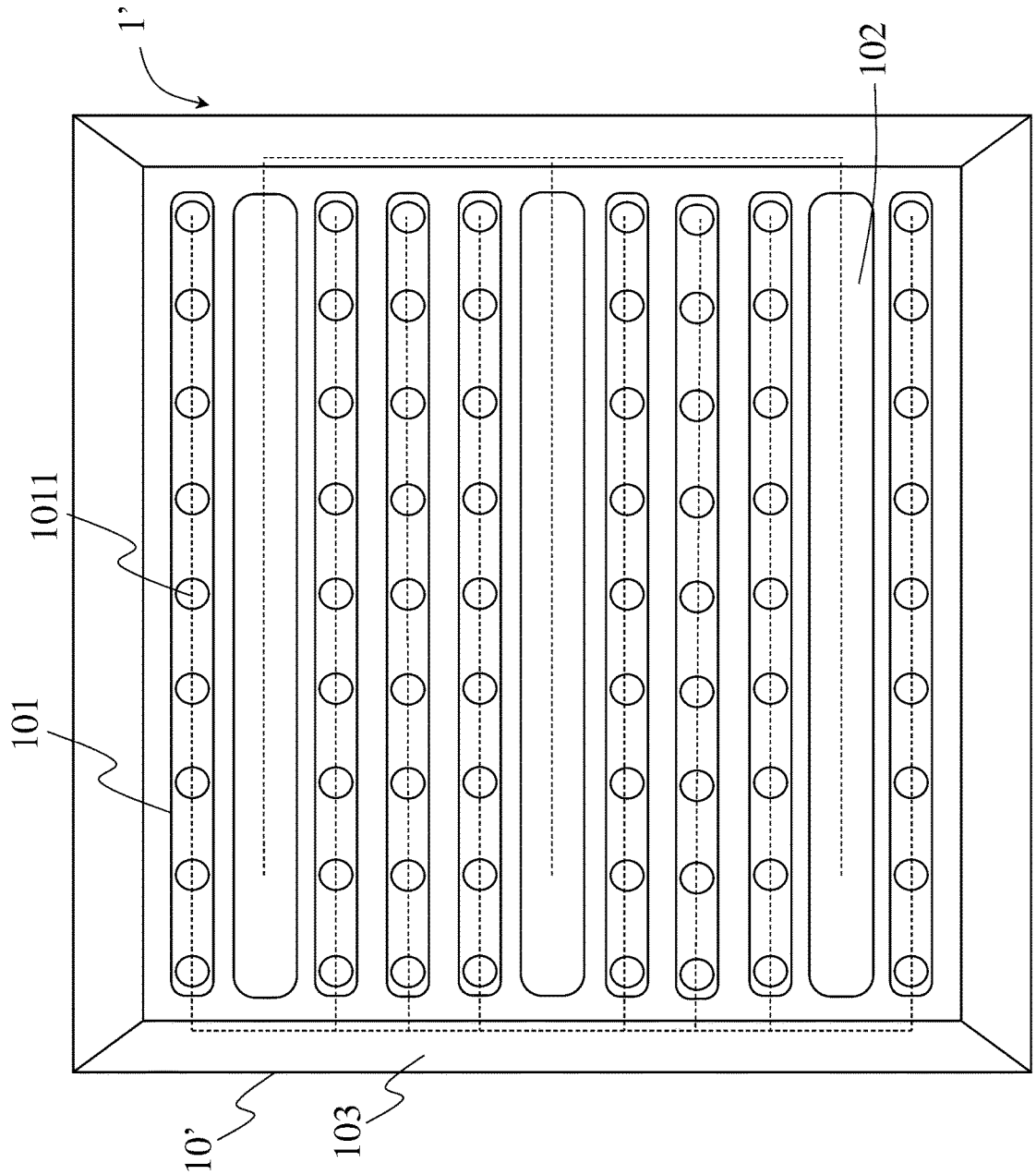
FIG. 8 is a schematic diagram of another lamp panel of an illumination lamp system having automatic switching function for sterilization according to another embodiment of the present invention.
Figure 9:
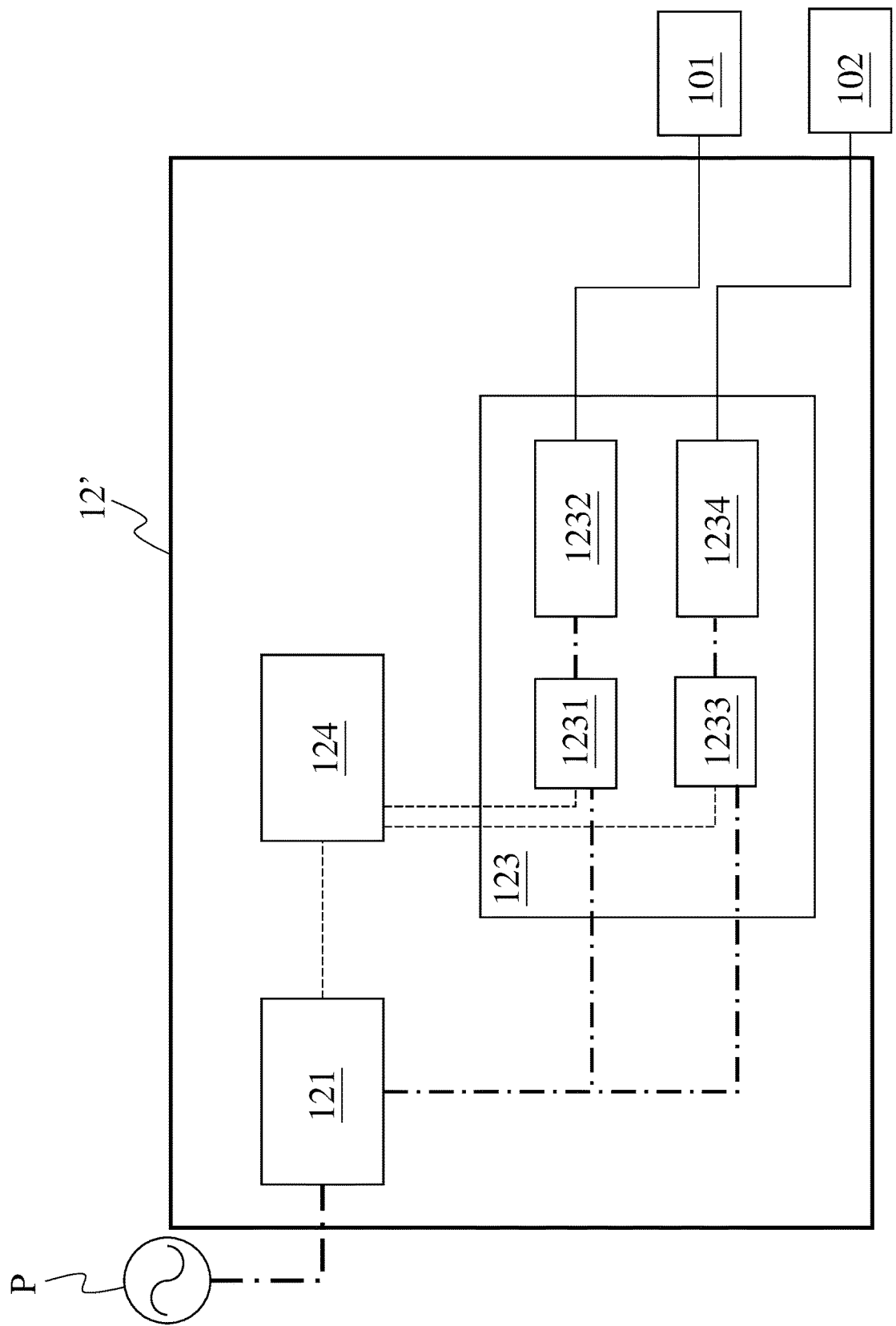
FIG. 9 is a circuit diagram of some parts of the aforementioned illumination lamp system having automatic switching function for sterilization.

FIG. 8 is a schematic diagram of another lamp panel of an illumination lamp system having automatic switching function for sterilization according to another embodiment of the present invention, FIG. 9 is a circuit diagram of some parts of the aforementioned illumination lamp system having automatic switching function for sterilization. To simplify the description, the components used in the previous embodiment will also be used in this embodiment. The same component symbol represents the same component. The illumination lamp system having automatic switching function for sterilization with semi-automatic structure includes a number of germicidal lighting lamp assemblies 1'. Each germicidal lighting lamp assembly 1' includes a lamp panel 10' and a control module 12'. A plurality of illumination LED strips 101 (comprising a number of visible LEDs 1011) and at least one ultraviolet germicidal light source 102 are arranged on one side of the lamp panel 12'. 4 light guide plates 103 are protruding outward and formed around the lamp panel 12'. Different from the previous embodiment, the ultraviolet germicidal light source 102 is a strip ultraviolet germicidal lamp. 3 ultraviolet germicidal light sources 102 are used in the lamp panel 12' and interspersed in 8 illumination LED strips 101.

The control module 12' is installed on the other side of the lamp panel 10', having the same components as in the control module 12 of the previous embodiment: the power conversion unit 121, the startup circuit 123 and the first microcontroller 124. Obviously, there is no infrared human body sensor and synchronization interface in this embodiment. Therefore, the illumination lamp system having automatic switching function for sterilization with semi-automatic structure will not detect if anyone enters the sterilization space, but process sterilization with the ultraviolet germicidal light sources emitting according to a preset sterilization time. In this way, although there is a danger of irradiating ultraviolet rays to people, the cost of this semi-automatic structure will be lower than that of the fully automatic structure if personnel control is carried out well.

The power conversion unit 121 is electrically connected to a power switch P externally. When the power switch P is turned on, the power conversion unit 121 receives AC power from the power switch P and performs voltage reduction and conversion to obtain a working AC power and a working DC power. This is the same as the previous example. The startup circuit 123 is electrically connected to the power conversion unit 121, the illumination LED strips 101 and the at least one ultraviolet germicidal light source 102, receiving the working AC power to drive the illumination LED strips 101 and the at least one ultraviolet germicidal light source 102 to light on. Functions are the same. As for the detailed structure of the startup circuit 123, please refer to FIG. 2 to FIG. 4 and related descriptions. It will not repeat here.

The first microcontroller 124 and that in the previous embodiment are actually the same hardware, electrically connected to the power conversion unit 121 and the startup circuit 123. The difference is that the first microcontroller 124 used in this embodiment is programmed to receive the working DC power to perform the following different tasks: driving the illumination LED strips 101 to light on via the startup circuit 123 when the power switch P is on (start/reset operation); when the power switch P is turned off and turned on within 3 seconds in an on state, turning off the illumination LED strips 101 and driving the at least one ultraviolet germicidal light source 102 to light on for a set time via the startup circuit 123 (sterilization operation); and when the at least one ultraviolet germicidal light source 102 has been lighted for the set time, turning off the at least one ultraviolet germicidal light source 102 and driving the illumination LED strips 101 to light on via the startup circuit 123. The set time is a specified continuous time, for example, 2 hours, for the ultraviolet germicidal light sources 102 to light on. It won't stop due to someone showing up. Lighting of the ultraviolet germicidal light sources 102 is driven by the external power switch P being turned on twice within 3 seconds. The illumination lamp system having automatic switching function for sterilization with semi-automatic structure has no additional built-in boot device. Since there is no synchronization interface, all ultraviolet germicidal light sources 102 of the germicidal lighting lamp assemblies 1' are uniformly controlled and driven by the power switch P.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. An illumination lamp system having automatic switching function for sterilization, comprising a plurality of germicidal lighting lamp assemblies, characterized in that each germicidal lighting lamp assembly comprises:

a lamp panel, having a plurality of illumination LED strips and at least one ultraviolet germicidal light source arranged on one side, and a plurality of light guide plates protruding outward formed around;

an infrared human body sensor, fixed on the outermost edge of one of the light guide plates, being actuated to detect infrared light sources within a detection range and determining whether someone exists based on the detection results; and a control module, installed on the other side of the lamp panel, comprising:

a power conversion unit, electrically connected to a power switch externally, receiving AC power from the power switch and performing voltage reduction and conversion to obtain a working AC power and a working DC power when the power switch is turned on;

a synchronization interface, electrically connected to a synchronization interface of a control module in other germicidal lighting lamp assemblies, keeping a synchronous voltage between a first electric potential and a second electric potential;

a startup circuit, electrically connected to the power conversion unit, the illumination LED strips and the at least one ultraviolet germicidal light source, receiving the working AC power to drive the illumination LED strips and the at least one ultraviolet germicidal light source to turn on; and a first microcontroller, electrically connected to the infrared human body sensor, the power conversion unit and the synchronization interface, receiving the working DC power to perform the following tasks:

driving the illumination LED strips to turn on via the startup circuit, and keeping the synchronous voltage at the first electric potential;

after the illumination LED strips have been turned on for a first waiting time, turning off the illumination LED strips and driving the at least one ultraviolet germicidal light source to turn on via the startup circuit, actuating the infrared human body sensor to detect, and changing the synchronous voltage to the second electric potential;

when the infrared human body sensor determines that there is someone, turning off the at least one ultraviolet germicidal light source and driving the illumination LED strips to turn on via the startup circuit, and changing the synchronous voltage to the first electric potential; and when the infrared human body sensor determines that there is no one and after the illumination LED strips have been turned on for the first waiting time, turning off the illumination LED strips and driving the at least one ultraviolet germicidal light source to turn on via the startup circuit, and changing the synchronous voltage to the second electric potential, wherein, when the synchronous voltage of the synchronization interface of any one of the germicidal lighting lamp assemblies is changed from the second electric potential to the first electric potential, the synchronous voltage of the synchronization interface of other germicidal lighting lamp assemblies is changed accordingly.

2. The illumination lamp system having automatic switching function for sterilization according to claim 1, wherein the at least one ultraviolet germicidal light source is an ultraviolet LED light bar, a strip ultraviolet germicidal lamp or a ring ultraviolet germicidal lamp.

3. The illumination lamp system having automatic switching function for sterilization according to claim 1, wherein the startup circuit further comprises:

a first relay, electrically connected to the first microcontroller and the power conversion unit, controlled by the first microcontroller to switch to transmit the working AC power;

a first illumination LED strip driver, electrically connected to the first relay and the illumination LED strips, regulating the working AC power to drive the illumination LED strips to turn light-on;

a second relay, electrically connected to the first microcontroller and the power conversion unit, controlled by the first microcontroller to switch to transmit the working AC power; and a first ultraviolet germicidal light source driver, electrically connected to the second relay and the at least one ultraviolet germicidal light source, regulating the working AC power to drive the at least one ultraviolet germicidal light source to turn on.

4. The illumination lamp system having automatic switching function for sterilization according to claim 1, wherein the startup circuit further comprises:

a third relay, electrically connected to the first microcontroller and the power conversion unit, controlled by the first microcontroller to switch to transmit the working AC power;

a second illumination LED strip driver, electrically connected to the third relay and the illumination LED strips, regulating the working AC power to drive the illumination LED strips to turn on; and a second ultraviolet germicidal light source driver, electrically connected to the third relay and the at least one ultraviolet germicidal light source, regulating the working AC power to drive the at least one ultraviolet germicidal light source to turn on, wherein the third relay only transmits the working AC power to one of the second illumination LED strip driver and the second ultraviolet germicidal light source driver.

5. The illumination lamp system having automatic switching function for sterilization according to claim 4, wherein the startup circuit further comprises:

a driver, electrically connected to the power conversion unit, converting the working AC power to a driving DC power which is able to drive the illumination LED strips or the at least one ultraviolet germicidal light source to light on; and a fourth relay, electrically connected to the first microcontroller, the driver, the illumination LED strips and the at least one ultraviolet germicidal light source, controlled by the first microcontroller to switch to transmit the working AC power to the illumination LED strips or the at least one ultraviolet germicidal light source.

6. The illumination lamp system having automatic switching function for sterilization according to claim 1, wherein each germicidal lighting lamp assembly further comprises an output and input connection interface, electrically connected to the first microcontroller, signally connecting to a control device externally for adjusting functions of the first microcontroller by the control device.

7. The illumination lamp system having automatic switching function for sterilization according to claim 6, wherein the output and input connection interface is a USB connector, a RJ10 connector, a RJ45 connector or an infrared signal transceiver module.

8. The illumination lamp system having automatic switching function for sterilization according to claim 6, wherein the first microcontroller is controlled by the control device to perform the following tasks:

setting a scheduled running time for the at least one ultraviolet germicidal light source;

setting a total luminous time of the at least one ultraviolet germicidal light source in the scheduled running time; and setting electrical connection between one synchronization interface and the synchronization interface of the control module in other germicidal lighting lamp assembly to create a group, or cutting off electrical connection of synchronization interfaces of the control modules of the germicidal lighting lamp assemblies to abolish an existing group, wherein the first microcontroller further turns off the at least one ultraviolet germicidal light source and drives the illumination LED strips to turn light on via the startup circuit, and changes the synchronous voltage to the first electric potential after the total luminous time of the at least one ultraviolet germicidal light source in the scheduled running time has passed.

9. The illumination lamp system having automatic switching function for sterilization according to claim 8, wherein the scheduled running time is greater than or equal to 2 hours.

10. The illumination lamp system having automatic switching function for sterilization according to claim 8, wherein the first microcontroller of each germicidal lighting lamp assembly further stores a serial number.

11. The illumination lamp system having automatic switching function for sterilization according to claim 10, further comprising a control circuit, electrically connected to the first microcontroller of each germicidal lighting lamp assembly, detecting the serial number of each germicidal lighting lamp assembly, checking whether the germicidal lighting lamp assembly is in one group, and sending the results of detection to a monitor signally connected thereto.

12. The illumination lamp system having automatic switching function for sterilization according to claim 8, wherein the first microcontroller of each germicidal lighting lamp assembly further stores operation sequence of the at least one ultraviolet germicidal light source.

13. The illumination lamp system having automatic switching function for sterilization according to claim 6, wherein the control device further comprises:
   at least one signal connection interface, signally connected to the output and input connection interface;
   a display screen;
   an input module;
   a plurality of status indicators; and
   a second microcontroller, electrically connected to the at least one signal connection interface, the display screen, the input module and the plurality of status indicators, showing functions and options thereof of the first microcontroller required to be adjusted on the display screen, setting the options of the functions of the first microcontroller that need to be adjusted via the input module, sending the options of the functions of the first microcontroller that need to be adjusted to the first microcontroller via the at least one signal connection interface, and showing current usage status of the control device via the status indicators.

14. The illumination lamp system having automatic switching function for sterilization according to claim 6, wherein a data receiving indicator is installed on the lamp panel, the data receiving indicator is electrically connected to the first microcontroller, and when the first microcontroller receives data via the output and input connection interface, the first microcontroller activates the data receiving indicator.

15. The illumination lamp system having automatic switching function for sterilization according to claim 1, wherein the synchronization interface is a power line contact.

16. The illumination lamp system having automatic switching function for sterilization according to claim 1, further comprising a personnel counter, signally connected to the first microcontroller of the control module, counting the number of people in the space where all germicidal lighting lamp assemblies are located.

17. The illumination lamp system having automatic switching function for sterilization according to claim 16, wherein if a count of the personnel counter increases while the synchronous voltage still remains at the second electric potential, the first microcontroller turns off the at least one ultraviolet germicidal light source and drives the illumination LED strips to light on via the startup circuit, and changes the synchronous voltage to the first electric potential.

18. The illumination lamp system having automatic switching function for sterilization according to claim 1, further comprising an ultraviolet indicator, signally connected to the first microcontroller of the control module, wherein when the ultraviolet germicidal light sources are turned on, the first microcontroller activates the ultraviolet indicator.

* * * * *